(12) United States Patent
Millefanti et al.

(10) Patent No.: US 9,868,684 B2
(45) Date of Patent: Jan. 16, 2018

(54) METHOD FOR MANUFACTURING PERFLUOROVINYLETHERS

(75) Inventors: Stefano Millefanti, Carbonate Como (IT); Vito Tortelli, Milan (IT); Giuseppe Marchionni, Milan (IT); Stefania Albonetti, Imola (IT); Manuel Gregori, Meldola (IT); Giuseppe Fornasari, Bologna (IT)

(73) Assignee: SOLVAY SPECIALTY POLYMERS ITALY S.P.A., Bollate (Milan) (IT)

( * ) Notice: Subject to any disclaimer, the term of this patent is extended or adjusted under 35 U.S.C. 154(b) by 29 days.

(21) Appl. No.: 13/982,288

(22) PCT Filed: Feb. 2, 2012

(86) PCT No.: PCT/EP2012/051730
§ 371 (c)(1),
(2), (4) Date: Jul. 29, 2013

(87) PCT Pub. No.: WO2012/104365
PCT Pub. Date: Aug. 9, 2012

(65) Prior Publication Data
US 2013/0324769 A1    Dec. 5, 2013

(30) Foreign Application Priority Data
Feb. 4, 2011 (EP) ...................... 11153426

(51) Int. Cl.
*C07C 41/24* (2006.01)
(52) U.S. Cl.
CPC .................. *C07C 41/24* (2013.01)
(58) Field of Classification Search
CPC ..................................... C07C 41/24
See application file for complete search history.

(56) References Cited

U.S. PATENT DOCUMENTS

| | | | |
|---|---|---|---|
| 4,340,750 A | 7/1982 | Yamabe et al. | |
| 5,821,394 A | 10/1998 | Schoebrechts et al. | |
| 2005/0038302 A1 | 2/2005 | Hedrick et al. | |
| 2007/0203368 A1 | 8/2007 | Tortelli et al. | |

FOREIGN PATENT DOCUMENTS

| | | | |
|---|---|---|---|
| EP | 0 459 463 A1 | 4/1991 | |
| EP | 0 471 320 A1 | 2/1992 | |
| EP | 1 719 750 A2 | 8/2006 | |
| JP | H04-099738 A | 3/1992 | |
| JP | H04-117333 A | 4/1992 | |
| JP | 8-502248 A | 3/1996 | |
| JP | 2006-312637 A | 11/2006 | |
| WO | 94/07827 A1 | 4/1994 | |
| WO | WO 9616003 A1 | 5/1996 | |
| WO | WO 2009150091 A1 | 12/2009 | |

OTHER PUBLICATIONS

Lunin et al. (Reviews: "Catalytic hydrodehalogenation of organic compounds", Russian Chemical Bulletin, vol. 45, No. 7, Jul. 199, pp. 1519-1534).*
Urbano F. et al.—"Hydrogenolysis of organohalogen compounds over palladium supported catalysts", (2001) Journal of Molecular Catalysis A : Chemical, vol. 173, No. 1-2, pp. 329-345, 17 pages, Sep. 10, 2001.

* cited by examiner

*Primary Examiner* — Rosalynd A Keys
(74) *Attorney, Agent, or Firm* — Osha Liang LLP

(57) ABSTRACT

The invention pertains to a process for the manufacture of a perfluorovinylether by hydrodehalogenation of a halofluoroether (HFE) having general formula (I-A) or (I-B):

RfO—CRf'X—CRf''Rf'''X''    (I-A)

wherein Rf represents a C1-C6 perfluoro(oxy)alkyl group; Rf', Rf'' and Rf''', equal or different from each other, independently represent fluorine atoms or C1-C5 perfluoro(oxy)alkyl groups; X and X', equal or different from each other, are independently chosen among Cl, Br or I;

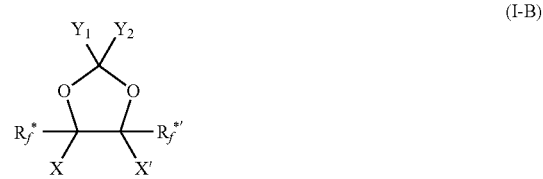

(I-B)

wherein Rf* and Rf*', equal or different from each other, independently represent fluorine atoms or C1-C3 perfluoro(oxy)alkyl groups; Y1 and Y2, equal or different from each other, independently represent fluorine atoms or C1-C3 perfluoroalkyl groups; X and X' are as above defined;
said process comprising contacting said halofluoroether (HFE) with hydrogen in the presence of a catalyst comprising palladium and at least one transition metal (M) selected from the group consisting of the metals of group VIIIB, other than palladium, and of group IB.

13 Claims, No Drawings

METHOD FOR MANUFACTURING PERFLUOROVINYLETHERS

CROSS-REFERENCE TO RELATED APPLICATIONS

This application is a U.S. national stage entry under 35 U.S.C. § 371 of International Application No. PCT/EP2012/051730 filed Feb. 2, 2012, which claims priority to EP Application No. 11153426.9 filed on Feb. 4, 2011 the whole content of this application being incorporated herein by reference for all purposes.

TECHNICAL FIELD

The present invention relates to a process for the hydrodehalogenation of halofluoroethers to perfluorovinylethers.

BACKGROUND ART

Perfluorovinylethers are useful monomers for the manufacture of various fluoropolymers, in particular thermoprocessable tetrafluoroethylene-based plastics and fluoroelastomers.

Methods for manufacturing perfluorovinylethers from halofluoroethers are known in the art. Generally known methods involve dehalogenation of suitable halofluoroether precursors in liquid phase in the presence of transition metals.

For instance, US 2007203368 (SOLVAY SOLEXIS SPA) 30 Aug. 2007 discloses a liquid-phase process for the manufacture of perfluorovinylethers by dehalogenation of certain halofluoroethers in the presence of transition metals as zinc, copper, manganese or metal couples as Zn/Cu, Zn/Sn, Zn/Hg. Liquid phase processes generally suffer from the disadvantage that significant amounts of metal halides solutions or muds are typically obtained as by-products (e.g. $ZnCl_2$ solutions/muds are produced when a chlorofluoroether is dechlorinated over zinc). Separation of said by-products from target perfluorovinylethers and their handling and disposal are time-consuming, costly and very burdensome from an industrial point of view, as these muds are highly corrosive and possibly endowed with negative environmental impact.

On the other hand, WO 2009/50091 (SOLVAY SOLEXIS SPA) 17 Dec. 2009 discloses a gas-phase process for the manufacture of a perfluorovinylether by hydrodehalogenation of a halofluoroether. Said process comprises contacting the halofluoroether with hydrogen in the presence of a catalyst comprising at least one transition metal of group VIII B at a temperature of at most 340° C. The process proceeds with high selectivity and without the formation of by-products which are difficult to handle.

Now the Applicant has surprisingly found that when the catalyst used in said gas-phase process comprises palladium and at least a second transition metal selected from group VIIIB and group IB metals the activity of the catalyst used in the hydrodehalogenation process may be retained for a longer period of time, thus increasing the economic profitability of the process.

The use of bimetallic catalysts in hydrodehalogenation reactions has been previously disclosed. For instance URBANO, F. J., et al. Hydrogenolysis of organohalogen compounds over palladium supported catalysts. *J. Molecular Catalysis A: Chemical*. 2001, vol. 173, p. 329-345. provides an overview of catalytic systems but it does not provide a specific disclosure of any catalyst compositions specifically suited for the hydrodehalogenation of halofluoroethers.

US 20050038302 A (HEDRICK ET AL.) 17 Feb. 2005 and EP 793633 B (SOLVAY SA) 17 Mar. 1999 similarly do not provide any teaching relating to the hydrodehalogenation of halofluoroethers.

DISCLOSURE OF INVENTION

It is thus an object of the present invention a process for the manufacture of a perfluorovinylether by hydrodehalogenation of a halofluoroether (HFE) having general formula (I-A) or (I-B):

   (I-A)

wherein $R_f$ represents a $C_1$-$C_6$ perfluoro(oxy)alkyl group; $R_f'$, $R_f''$ and $R_f'''$, equal or different from each other, independently represent fluorine atoms or $C_1$-$C_5$ perfluoro(oxy)alkyl groups; X and X', equal or different from each other, are independently chosen among Cl, Br or I;

   (I-B)

wherein $R_f^*$ and $R_f^{*'}$, equal or different from each other, independently represent fluorine atoms or $C_1$-$C_3$ perfluoro(oxy)alkyl groups; $Y_1$ and $Y_2$, equal or different from each other, independently represent fluorine atoms or $C_1$-$C_3$ perfluoroalkyl groups; X and X' are as above defined; said process comprising contacting said halofluoroether (HFE) with hydrogen in the presence of a catalyst comprising palladium and at least one transition metal selected from the group consisting of the metals of group VIIIB other than palladium and of group IB.

The Applicant has found that by using a catalyst comprising said composition of transition metals it is advantageously possible to successfully isolate perfluorovinylethers with high selectivities and with lower deactivation rates of the catalyst with respect to the previously known catalyst.

The process of the present invention enables to selectively obtain perfluorovinylethers of formulae (A*) and (B*), respectively:

   (A*)

   (B*)

wherein $R_f$, $R_f'$, $R_f''$, $R_f'''$, $Y_1$, $Y_2$, $R_f^*$ and $R_f^{*'}$ have same meanings as above defined without the need to frequently regenerate the catalyst at high temperature with $H_2$ due to its high stability.

The process is carried out at temperatures generally not exceeding 340° C., thus poisoning from HF, sintering or coking phenomena otherwise known as significantly reducing the life of group VIIIB transition metal catalysts can be essentially avoided.

The term "hydrodehalogenation", as used therein, is intended to denote the selective elimination of two halogen atoms, X, X' in formulae (I-A) an (I-B), chosen among Cl, Br or I from two adjacent fluorine-substituted carbon atoms of said halofluoroether (HFE), in the presence of hydrogen, to yield the corresponding perfluorovinylether.

The expression "perfluoro(oxy)alkyl group" is intended to indicate either a perfluoroalkyl group or a perfluorooxyalkyl group, that is a perfluoroalkyl group comprising one or more than one catenary oxygen atom.

According to a first embodiment of the invention, the halofluoroether (HFE) of the invention is a chlorofluoroether (HFE-1) having general formula (I-A) as described above, wherein X and X', equal or different from each other, are independently chosen among Cl, Br or I, with the proviso that at least one of X and X' in said formula (I-A) is a chlorine atom.

The halofluoroether (HFE) of this first embodiment is preferably a chlorofluororoether (HFE-2) having general formula (I-A) as described above, wherein X and X' are equal to each other and are chlorine atoms, that is to say that chlorofluoroether (HFE-2) complies with formula (II-A) here below: $R_fO-CR_f'Cl-CR_f''R_f'''Cl$ (II-A)
wherein:
$R_f$ represents a $C_1$-$C_6$ perfluoro(oxy)alkyl group, preferably a $C_1$-$C_4$ perfluoroalkyl group, more preferably a $C_1$-$C_3$ perfluoroalkyl group;
$R_f'$, $R_f''$ and $R_f'''$, equal or different from each other, independently represent fluorine atoms or $C_1$-$C_5$ perfluoro(oxy)alkyl groups, preferably fluorine atoms or $C_1$-$C_3$ perfluoroalkyl groups, more preferably fluorine atoms or $C_1$-$C_2$ perfluoroalkyl groups, even more preferably fluorine atoms.

The chlorofluoroether (HFE-2) of the present invention is typically a gaseous compound under process conditions.

Representative compounds of chlorofluoroethers (HFE-2) described by formula (II-A) useful in the present invention include, but are not limited to, the following compounds:
$CF_3OCFClCF_2Cl$, $CF_3CF_2OCFClCF_2Cl$, $CF_3CF_2CF_2OCFClCF_2Cl$, $CF_3OCF_2OCFClCF_2Cl$, $CF_3CF_2OCF_2OCFClCF_2Cl$, $CF_3OCF_2CF_2OCF_2OCFClCF_2Cl$.

According to a second embodiment of the invention, the halofluoroether (HFE) of the invention is a chlorofluorodioxolane (HFE-3) having general formula (I-B) as described above, wherein X and X', equal or different from each other, are independently chosen among Cl, Br or I, with the proviso that at least one of X and X' in said formula (I-B) is a chlorine atom.

The halofluoroether (HFE) of this second embodiment is preferably a chlorofluorodioxolane (HFE-4) having general formula (I-B) as described above, wherein X and X' are equal to each other and are chlorine atoms, that is to say that chlorofluorodioxolane (HFE-4) complies with formula (II-B) here below:

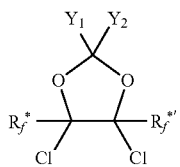

(II-B)

wherein $R_f^*$ and $R_f^{*'}$, equal or different from each other, independently represent fluorine atoms or $C_1$-$C_3$ perfluoro(oxy)alkyl groups, preferably fluorine atoms or $C_1$-$C_3$ perfluorooxyalkyl groups, more preferably fluorine atoms or $-OCF_3$ groups; $Y_1$ and $Y_2$, equal or different from each other, independently represent fluorine atoms or $C_1$-$C_3$ perfluoroalkyl groups, preferably fluorine atoms.

The chlorofluorodioxolane (HFE-4) of the present invention is typically a gaseous compound under process conditions.

Representative compounds of chlorofluorodioxolanes (HFE-4) described by formula (II-B) useful in the present invention include, but are not limited to, the following compounds:

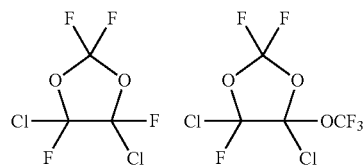

The process of the present invention is carried out in the presence of a catalyst comprising palladium and at least one second transition metal M selected from the group consisting of the metals of group VIIIB, other than palladium, and of group IB.

For the avoidance of doubt, the term "transition metal of group VIIIB" is hereby intended to denote the following metals: Fe, Ru, Os, Co, Rh, Ir, Ni, Pd, Pt.

For the avoidance of doubt, the term "transition metal of group IB" is hereby intended to denote the following metals: Cu, Ag, Au.

Among preferred group VIIIB transition metals to be used as the at least second transition metal M in the catalyst composition, mention can be made of Ru and Pt.

Preferably, the catalyst comprises Pd and at least one second transition metal M selected from the group consisting of the group IB metals. More preferably, the second transition metal M is Cu or Au.

The molar ratio Pd:M between Pd and the at least one second transition metal M in the catalyst ranges from 5:1 to 1:6, typically it ranges from 2:1 to 1:5, preferably from 1.5:1 to 1:4. The ratio may even advantageously be from 1.5:1 to 1:3.

When metal M is selected among metals of group IB typical molar ratios Pd:M range from 2:1 to 1:6, preferably from 1.5:1 to 1:5.

The catalyst of the invention typically is a supported catalyst, that is to say that it comprises the composition of transitions metals as above described and an inert carrier.

The inert carrier is generally selected from carbon, silica and alumina, preferably from carbon. Suitable inert carriers generally have a BET surface area of from 800 to 1600 m²/g, preferably from 1000 to 1600 m²/g, even more preferably from 1100 to 1500 m²/g.

The BET surface area is measured by $N_2$ adsorption as per the Brunauer, Emmett and Teller method of calculation, according to ISO 9277.

When supported, the catalyst generally comprises Pd in an amount of from 0.1 wt % to 2 wt %, preferably from 0.3 wt % to 1.8 wt %, more preferably from 0.5 wt % to 1.5 wt %.

The amount of the at least one second metal M in the supported catalyst is determined, on the basis of the weight of palladium, in order to obtain a Pd:M molar ratio falling within the above identified ranges of from 5:1 to 1:6.

The catalyst used in the inventive process may be prepared according to conventional methods.

When supported, the catalyst may be advantageously prepared by the incipient wetness impregnation method. In such a method an aqueous solution of a suitable metal precursor is added to the inert carrier and dried. The metal is then typically reduced by treatment with $H_2$. Among suitable precursors mention can be made of the transition metal halides.

In the preparation of the catalyst to be used in the inventive process impregnation of the inert carrier with the at least two transition metals may be carried out either sequentially or simultaneously. In a sequential process the inert carrier is first impregnated with a solution of one of the transition metals, optionally dried and then impregnated with a solution of the at least one second transition metal. In a simultaneous process the inert carrier is impregnated with a solution comprising both transition metals, followed by drying and reduction, if needed.

Catalysts used in the process of the invention are generally activated before use by pre-reduction under hydrogen at temperatures comprised between 250° C. and 450° C., more preferably between 250° C. and 400° C., even more preferably between 300° C. and 400° C.

Typically, regeneration of the catalyst is also carried out under hydrogen at temperatures comprised between 300° C. and 500° C., more preferably between 350° C. and 500° C., even more preferably between 400° C. and 500° C. The term regeneration refers to the process of restoring the catalytic activity of the catalyst which has been deactivated by use in the hydrodehalogenation process.

Good results have been obtained with catalysts comprising Pd and Ru supported on carbon, wherein the molar ratio between Pd and Ru ranges from 1:1 to 1:4. These catalysts maintain unaltered catalytic performances (in terms of conversion and selectivity) up to 80 hours on stream. As shown in the appended Examples, catalysts comprising Ru only supported on carbon undergo a significant decrease in conversion already at 50 hours on stream.

On the other hand Pd catalysts supported on carbon, when tested in the hydrodehalogenation of the same halofluoroether, show in general a much lower selectivity towards the desired perfluorovinylether than the Pd-M catalyst of the invention (50% vs. 80-95%).

The expression "time on stream" is hereby defined as the duration of continuous operations between successive reactor shut down for catalyst regeneration.

Good results have been obtained with also with catalysts comprising Pd and Au supported on carbon, wherein the molar ratio between Pd and Au ranges from 1:1 to 1:4. It has been found that these catalysts maintain unaltered good catalytic performances up to 80 hours on stream.

Even better results have been obtained with catalysts comprising Pd and Cu supported on carbon, wherein the molar ratio between Pd and Cu ranges from 1:1 to 1:4, even from 1:1 to 1:3. These catalysts maintain unaltered catalytic performances even up to 110 hours on stream.

The process of the present invention is preferably carried out at a temperature of at most 340° C.

The Applicant has found that for obtaining perfluorovinylethers in high yields it is generally advantageous to carry out the process at temperatures not exceeding 340° C. Without being bound by theory the Applicant believes that the decrease of selectivity observed when the temperature exceeds 340° C. may be due to the decomposition of the halofluoroether (HFE).

Lower limits of temperatures suitable for achieving efficient conversion of halofluoroethers to perfluorovinylethers are not particularly limited. Temperatures of advantageously at least 190° C., preferably at least 200° C., more preferably at least 210° C., and even more preferably at least 230° C. are generally used. Best results have been obtained at temperatures comprised between 230° C. and 320° C.

The process of the present invention is advantageously carried out in gas-phase, that is to say in conditions wherein hydrogen and both the halofluoroether (HFE) and corresponding perfluorovinylether are in gaseous state. It is nevertheless understood that the catalyst is generally used as a solid, so that the reaction takes place between reactants in the gas phase and catalyst in the solid state.

Hydrogen can be fed either as neat reactant or diluted with an inert gas, e.g. nitrogen, helium or argon.

The process of the invention is carried out in any suitable reactor, including fixed and fluidized bed reactors. The process is generally carried out in continuous using a plug flow reactor comprising a fixed bed of catalyst.

The reaction pressure is not critical to the process. The process of the present invention is typically carried out under atmospheric pressure, even though pressures between 1 and 3 bar can be employed.

Contact time between the halofluoroether (HFE) and the catalyst is not particularly limited and will be chosen by the skilled in the art in relation, notably, with reaction temperature and other process parameters. Contact time, which, for continuous processes, is defined as the ratio of the catalyst bed volume to the gas flow rate in standard conditions at 0° C. and 1 bar, may vary between a few seconds and several hours. Nevertheless, it is understood that this contact time is generally comprised between 2 and 200 seconds, preferably between 5 and 150 seconds.

For continuously operated processes, time on stream may vary between 5 and 500 hours, preferably between 10 and 200 hours. A time on stream of at least 50 hours without a significant decrease of conversion may generally be advantageous. Even more advantageous might be a time on stream of at least 50 hours without a significant decrease of both conversion and selectivity. It is also understood that spent catalyst can be advantageously regenerated as above mentioned and recycled in a further time on stream in the process of the invention.

Good conversions are generally obtained in the presence of a hydrogen/halofluoroether (HFE) molar ratio comprised between 0.8 and 4, preferably between 0.8 and 3, more preferably between 0.8 and 2.

It has been found that conversion typically increases by increasing the hydrogen/halofluoroether (HFE) molar ratio up to 4. A hydrogen/halofluoroether (HFE) molar ratio greater than 4 could be used but it does not provide any additional increase in conversion and is usually uneconomical.

A halogenidric acid is obtained as a by-product from the process of the invention. When the halofluoroether (HFE) is selected from a chlorofluoroether (HFE-1), a chlorofluoroether (HFE-2), a chlorofluorodioxolane (HFE-3) or a chlorofluorodioxolane (HFE-4), hydrogen chloride is typically obtained; halogenidric acids can be easily recovered by neutralization in an aqueous alkaline solution or by absorption in water.

The invention will be now described in more detail with reference to the following examples whose purpose is merely illustrative and not limitative of the scope of the invention.

Should the disclosure of any patents, patent applications, and publications which are incorporated herein by reference conflict with the description of the present application to the extent that it may render a term unclear, the present description shall take precedence.

EXAMPLES

General Hydrodehalogenation Procedure

A continuous gas-phase catalytic process was carried out at atmospheric pressure in a plug-flow reactor. The overall reaction is illustrated by the following equation:

$$CF_3OCFClCF_2Cl + H_2 \rightarrow CF_3OCF=CF_2 + 2HCl$$

An amount of each catalyst equal to 1.0 g in all of the runs was loaded in a stainless steel tubular reactor having a length of 520 mm and an internal diameter of 10 mm. The catalyst bed was placed in the middle section of the reactor whereas the upper and lower sections thereof were filled with granular quartz. The catalyst was dried at 300° C. in flowing helium (5 Nl/h) for 4 hours and then cooled down to room temperature. The catalyst was then pre-reduced under a flow of hydrogen diluted with helium at 300° C. for one hour. The temperature was lowered to 250° C. and $CF_3OCFClCF_2Cl$ and a mixture of hydrogen and helium were continuously fed into the reactor.

The gaseous reactor mixture coming from the reaction was sampled and analyzed by GC and GC-MS for the determination of selectivity and conversion.

General Procedure for the Preparation of Pd-M Catalyst 50 g of extruded activated carbon NORIX RX3 EXTRA (Norit Nederland B.V.) having BET area of 1400 m²/g and 0.8 cm³/g pore volume, were crushed and sieved to obtain 20-40 mesh granules. Sieved carbon was dried under vacuum at 200° C. and then impregnated with incipient wetness method with an aqueous hydrochloridric solution of $PdCl_2$ and $CuCl_2.2H_2O$ in order to obtain three different catalysts (A, B and C) having different Pd:Cu molar ratios.

Each catalyst was dried at 120° C. for 6 h under a nitrogen flow and then reduced under $H_2$ at 300° C. for 1 h.

Following the same procedure sieved carbon was impregnated with an aqueous hydrochloridric solution of $PdCl_2$ and $HAuCl_4.3H_2O$ (catalyst D); an aqueous solution of $PdCl_2$ and $AgNO_3$ (catalyst E) or an aqueous hydrochloridric solution of $PdCl_2$ and $RuCl_3.3H_2O$ (catalyst F). Catalysts compositions are shown in Table 1.

TABLE 1

| Catalyst | M | Pd (wt %) | Pd:M (molar ratio) |
|---|---|---|---|
| A | Cu | 0.97 | 1:1 |
| B | Cu | 1.1 | 1:2 |
| C | Cu | 0.97 | 1:4 |
| D | Au | 0.96 | 1:2 |
| E | Ag | 0.97 | 1:1.1 |
| F | Ru | 1.04 | 1:4.1 |

Example 1

A sample of 1.0 g of each catalyst was loaded in the reactor and tested according to the general hydrodehalogenation procedure.

Before starting the reaction the catalyst was dried at 300° C. for 4 h and reactivated with $H_2$ at 300° C. for 1 h.

$CF_3OCFClCF_2Cl$ space velocity was 1.4 g/h $CF_3CFClCF_2Cl*g_{cat}^{-1}$ and residence time was 10 sec, the molar ratio between $H_2$ and $CF_3OCFClCF_2Cl$ was 1:1. Process temperature was 250° C. Conversion and selectivity were calculated via GC with internal standard method. Results are reported in Table 2.

TABLE 2

| Run # | Catalyst (M) | Time on stream (h) | Conversion % $CF_3OCFClCF_2Cl$ | Selectivity % $CF_3OCF=CF_2$ |
|---|---|---|---|---|
| 1 | A (Cu) | 50 | 75 | 84 |
| 2 | B (Cu) | 9 | 83 | 90 |
| 3 | B (Cu) | 51 | 89 | 93 |
| 4 | B (Cu) | 106 | 88 | 94 |
| 5 | C (Cu) | 50 | 88 | 96 |
| 6 | D (Au) | 50 | 83 | 94 |
| 7 | D (Au) | 79 | 81 | 95 |
| 8 | E (Ag) | 50 | 48 | 76 |
| 9 | F (Ru) | 9 | 78 | 76 |
| 10 | F (Ru) | 50 | 68 | 87 |
| 11 | F (Ru) | 80 | 67 | 90 |

Comparative Example 1

The same dried sieved carbon used in the preparation of catalysts A to F was used to prepare samples of catalyst comprising one transition metal of group VIIIB. The sieved carbon was impregnated with incipient wetness method with an aqueous hydrochloridric solution of $RuCl_3.3H_2O$ (catalyst G) or $PdCl_2$ (catalyst H) as shown in Table 3.

Each catalyst was dried at 120° C. for 6 h under a nitrogen flow and then reduced under $H_2$ at 300° C. for 1 h.

TABLE 3

| Catalyst | M | wt % |
|---|---|---|
| G | Ru | 1.1 |
| H | Pd | 1.0 |

A sample of 1.0 g of catalyst (G or H) was tested according to the general hydrodehalogenation procedure. $CF_3OCFClCF_2Cl$ space velocity was 1.4 g/h $CF_3CFClCF_2Cl*g_{cat}^{-1}$, residence time was 10 sec and temperature was 250° C. Molar ratio between $H_2$ and $CF_3OCFClCF_2Cl$ was 1:1. Results in are reported in Table 4.

TABLE 4

| Run # | Catalyst (M) | Time on stream (h) | Conversion % $CF_3OCFClCF_2Cl$ | Selectivity % $CF_3OCF=CF_2$ |
|---|---|---|---|---|
| 12 | G (Ru) | 10 | 40 | 70 |
| 13 | G (Ru) | 47 | 20 | 95 |
| 14 | G (Ru) | 70 | 10 | 97 |
| 15 | H (Pd) | 4 | 69 | 50 |

Comparing the results of Tables 2 (runs 9-11) with those of Table 4 runs 12-14), it can be appreciated that catalysts according to the invention, comprising Pd and Ru, maintain their catalytic activity (conversion and selectivity) unchanged up to 80 hours on stream whereas catalysts comprising Ru only supported on carbon show a visible reduction in conversion already after 50 hours on stream and an even greater decrease at longer times.

On the other hand catalysts comprising Pd alone supported on carbon have very low selectivity in the desired end product already at the beginning of the catalytic activity.

The invention claimed is:

1. A process for the manufacture of a perfluorovinylether by hydrodehalogenation of a halofluoroether (HFE) having general formula (I-A) or (I-B):

$$R_fO-CR_f'X-CR_f''R_f'''X' \quad \text{(I-A)}$$

wherein $R_f$ represents a $C_1$-$C_6$ perfluoro(oxy)alkyl group; $R_f'$, $R_f''$ and $R_f'''$, equal or different from each other, independently represent fluorine atoms or $C_1$-$C_5$ perfluoro(oxy)alkyl groups; X and X', equal to or different from each other, are independently selected from the group consisting of Cl, Br and I;

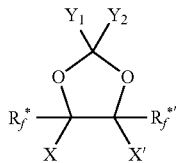
(I-B)

wherein $R_f^*$ and $R_f^{*'}$, equal to or different from each other, independently represent fluorine atoms or $C_1$-$C_3$ perfluoro(oxy)alkyl groups; $Y_1$ and $Y_2$, equal to or different from each other, independently represent fluorine atoms or $C_1$-$C_3$ perfluoroalkyl groups; X and X' are as above defined;

said process comprising the step of contacting said halofluoroether (HFE) with hydrogen in the presence of a catalyst, said catalyst comprising:
palladium;
at least one transition metal (M) selected from the group consisting of the metals of group VIIIB, other than palladium, and metals of group IB; and
an inert carrier,
wherein the molar ratio between palladium and the at least one transition metal (M) ranges from 2:1 to 1:5, and wherein the catalyst is prepared by a process where the inert carrier is impregnated with an aqueous solution comprising palladium and the at least one transition metal selected from ruthenium, copper and gold.

2. The process of claim 1, wherein the halofluoroether (HFE) is a chlorofluoroether (HFE-1) having general formula (I-A), wherein X and X', equal to or different from each other, are independently selected from the group consisting of Cl, Br and I, wherein that at least one of X and X' in said formula (I-A) is a chlorine atom.

3. The process of claim 1, wherein the halofluoroether (HFE) is a chlorofluoroether (HFE-2) having general formula (II-A):

$$R_fO-CR_f'Cl-CR_f''R_f'''Cl \quad \text{(II-A)}$$

wherein $R_f$ represents a $C_1$-$C_6$ perfluoro(oxy)alkyl group, $R_f'$, $R_f''$ and $R_f'''$, equal to or different from each other, independently represent fluorine atoms or $C_1$-$C_5$ perfluoro(oxy) alkyl groups.

4. The process of claim 1, wherein the inert carrier is carbon.

5. The process of claim 4, wherein the amount of palladium on the inert carrier ranges from 0.1 wt % to 2 wt %.

6. The process of claim 1, wherein the metal (M) is ruthenium.

7. The process of claim 1 wherein the metal is copper or gold.

8. The process of claim 1, said process being carried out at temperatures of at most 340° C.

9. The process of claim 1, said process being carried out at temperatures of at least 190° C.

10. The process of claim 1, wherein the hydrogen/halofluoroether (HFE) molar ratio is comprised between 0.8 and 4.

11. The process of claim 3, wherein $R_f$ represents a $C_1$-$C_4$ perfluoroalkyl group.

12. The process of claim 10, wherein the hydrogen/halofluoroether (HFE) molar ratio is comprised between 0.8 and 3.

13. The process of claim 12, wherein the hydrogen/halofluoroether (HFE) molar ratio is comprised between 0.8 and 2.

* * * * *